US009192567B2

(12) United States Patent
Rabinovich-Guilatt et al.

(10) Patent No.: US 9,192,567 B2
(45) Date of Patent: *Nov. 24, 2015

(54) METHOD FOR TREATING EYE DISEASE OR CONDITIONS AFFECTING THE POSTERIOR SEGMENT OF THE EYE

(75) Inventors: Laura Rabinovich-Guilatt, Paris (FR); Gregory Lambert, Chatenay-Malabry (FR)

(73) Assignee: SANTEN SAS, Evry (FR)

(*) Notice: Subject to any disclaimer, the term of this patent is extended or adjusted under 35 U.S.C. 154(b) by 1470 days.

This patent is subject to a terminal disclaimer.

(21) Appl. No.: 11/806,556

(22) Filed: Jun. 1, 2007

(65) Prior Publication Data

US 2007/0281913 A1  Dec. 6, 2007

Related U.S. Application Data

(62) Division of application No. 11/444,349, filed on Jun. 1, 2006, now abandoned.

(30) Foreign Application Priority Data

Jun. 1, 2006  (EP) ..................................... 06290901

(51) Int. Cl.
| A61K 9/51 | (2006.01) |
| A61K 38/00 | (2006.01) |
| A61K 31/56 | (2006.01) |
| A61K 31/74 | (2006.01) |
| A61K 9/00 | (2006.01) |
| A61K 31/4745 | (2006.01) |
| A61K 31/573 | (2006.01) |
| A61K 47/48 | (2006.01) |
| A61K 48/00 | (2006.01) |

(52) U.S. Cl.
CPC ............ *A61K 9/0014* (2013.01); *A61K 9/0048* (2013.01); *A61K 31/4745* (2013.01); *A61K 31/573* (2013.01); *A61K 47/48046* (2013.01); *A61K 48/00* (2013.01)

(58) Field of Classification Search
None
See application file for complete search history.

(56) References Cited

U.S. PATENT DOCUMENTS

| 4,340,594 A | 7/1982 | Mizushima et al. |
| 5,591,426 A | 1/1997 | Dabrowski et al. |
| 6,007,826 A | 12/1999 | Benita et al. |
| 6,432,439 B1 | 8/2002 | Suzuki et al. |
| 2005/0244469 A1 | 11/2005 | Whitcup et al. |
| 2006/0002963 A1* | 1/2006 | Rabinovich-Guilatt et al. ............................ 424/400 |
| 2006/0073182 A1* | 4/2006 | Wong et al. .................... 424/426 |
| 2006/0094700 A1 | 5/2006 | Lyons |
| 2006/0233859 A1 | 10/2006 | Whitcup et al. |
| 2007/0073182 A1 | 3/2007 | Wilson |
| 2010/0087413 A1* | 4/2010 | Wilckens ...................... 514/181 |

FOREIGN PATENT DOCUMENTS

| AU | 531588 B2 | 9/1983 |
| EP | 0244178 A2 | 11/1987 |
| EP | 0696452 A1 | 2/1996 |
| EP | 0878197 A1 | 11/1998 |
| EP | 1020194 A1 | 7/2000 |
| EP | 1864667 A1 | 12/2007 |
| JP | 1982016818 A | 1/1982 |
| JP | 1993132498 A | 5/1993 |
| JP | 899867 A | 4/1996 |
| JP | 1129483 A | 2/1999 |
| JP | 7504848 | 7/2000 |
| JP | 2007042262 A | 2/2007 |
| WO | 9001933 A1 | 3/1990 |
| WO | 9911270 A1 | 3/1999 |
| WO | WO 9911270 A1 * | 3/1999 |
| WO | 9916471 A1 | 4/1999 |
| WO | 03053405 A1 | 7/2003 |
| WO | 2004058272 A1 | 7/2004 |
| WO | 2005011741 A2 | 2/2005 |
| WO | 2005107727 A1 | 11/2005 |
| WO | 2006017347 A2 | 2/2006 |
| WO | 2006050836 A2 | 5/2006 |
| WO | 2006050838 A2 | 5/2006 |
| WO | 2007138113 A1 | 12/2007 |

OTHER PUBLICATIONS

Lingyun et al., Characterization of a Novel Intraocular Drug-Delivery System Using Crystalline Lipid Antiviral Prodrugs of Ganciclovir and Cyclic Cidofovir, Shiley Eye Center, Jun. 15, 2004.*
Schmidt et al. Pharmacokinetics of intravitreal 5-flluorouracil prodrugs in silicone oil: experimental studies in pigs, Acta Ophthalmologica Scandinavica 2005.*
Taskintuna et al. Evaluation of a novel lipid prodrug for intraocular drug delivery: effect of acyclovir diphosphate dimyristoylglycerol in a rabbit model with herpes simplex virus-1 retinitis, Retina 17:57-64, 1997.*
Synek et al., Transmission electron microscopy of the vitreous body tissue in chronic hemophthalmos, Vet. Med.-Czech, 50, 2005 (3): 136-138.*
Taskintuna et al., "Evaluation of a novel lipid prodrug for intraocular drug delivery: effect of acyclovir diphosphate dimyristoylglycerol in a rabbit model with herpes simplex virus-1 retinitis", Retina, 1997, vol. 17, No. 1, pp. 57-64.
Laugesen et al., "Pharmacokinetics of intravitreal 5-fluorouracil prodrugs in silicone oil: experimental studies in pigs", Acta Ophthalmologica Scandinavica, 2005, vol. 83, No. 2, pp. 184-190.
Yang et al., "An intravitreal sustained-release triamcinolone and 5-fluorouracil codrug in the treatment of experimental proliferative vitreoretinopathy", Archives of Ophthalmology, 1998, vol. 116, No. 1, pp. 69-77.

(Continued)

*Primary Examiner* — Michael G Hartley
*Assistant Examiner* — Nabila Ebrahim
(74) *Attorney, Agent, or Firm* — Young & Thompson

(57) ABSTRACT

Described is the use of prodrug for the manufacture of a medicament useful for treating an ocular disease affecting the posterior segment of the eye, in a subject in need thereof, wherein the prodrug is a composition injected into the vitreous body, and the frequency of injections does not exceed one injection per month.

10 Claims, No Drawings

(56) References Cited

OTHER PUBLICATIONS

Macha et al., "Ocular disposition of ganciclovir and its monoester prodrugs following intravitreal administration using microdialysis", Drug Metabolism and Disposition, 2002, vol. 30, No. 6, pp. 670-675.

Holekamp et al., "Intraocular sustained-release fluocinolone for uveitis", Optometry—Journal of the American optometric association, 2005, vol. 76, No. 10, p. 566.

Synek et al., "Transmission electron microscopy of the vitreous body tissue in chronic hemophthalmos", Vet. Med.-Czech, 2005, vol. 50, No. 3, pp. 136-138.

Das et al., "Intravitreal dexamethasone in exogenous bacterial endophthalmitis: results of a prospective randomised study", J. Ophthalmol., 1999, vol. 83, No. 9, pp. 1050-1055.

Civiale et al., "Ocular permeability screening of dexamethasone esters through combined cellular and tissue systems", J Ocul Pharmacol Ther., 2004, vol. 20, No. 1, pp. 75-84.

Benameur et al., "Liposome-incorporated dexamethasone palmitate inhibits in-vitro lymphocyte response to mitogen", J. Pharm. Pharmacol., 1995, vol. 47, No. 10, pp. 812-817.

Tamilvanan et al., "The potential of lipid emulsion for ocular delivery of lipophilic drugs", Eur. J. Pharma. Biopharma., 2004, vol. 58, No. 2, pp. 357-368.

Lallemand et al., "Cyclosporine a delivery to the eye: a pharmaceutical challenge", Eur. J. Pharma. Biopharma., 2003, vol. 56, No. 3, pp. 307-318.

European Search Report, dated Mar. 24, 2011, from corresponding EP application No. EP10177375.

European Search Report, dated Nov. 28, 2006, from corresponding EP application No. EP06290901.

European Search Report, dated Dec. 2, 2004, from corresponding EP application No. EP1611879.

International Search Report, dated Aug. 31, 2007, from corresponding PCT application No. PCT/EP2007/055413.

International Search Report, dated Mar. 30, 2009, from corresponding PCT application No. PCT/EP2008/066731.

\* cited by examiner

METHOD FOR TREATING EYE DISEASE OR CONDITIONS AFFECTING THE POSTERIOR SEGMENT OF THE EYE

The present invention involves the fields of ophthalmology, more precisely the treatment of eye disease or conditions, especially disease or condition affecting the posterior segment of the eye. A posterior ocular condition is a disease which primarily affects a posterior ocular site such as choroid or sclera, vitreous, vitreous chamber, retina, optic nerve, and blood vessels and nerves which vascularize or innervate a posterior ocular site.

The present invention relates to a method for in-vivo sustained release of an active agent through intraocular invasive delivery of a prodrug thereof.

Treatment of diseases or conditions affecting the posterior segment of the eye are complicated by the inaccessibility of the posterior eye to topically applied medications.

Treatments of posterior eye diseases require intravitreal or periocular injections or systemic drug administration. Local injections are usually preferred to systemic drug administration because the blood/retinal barrier impedes the passage of most drugs from the systemically circulating blood to the interior of the eye. Therefore large systemic doses are needed to treat eye posterior diseases, which often result in systemic toxicities.

There are diseases for which periocular injections do not allow the delivery of efficacious amounts to the target sites. For these diseases, intravitreal injections are found necessary. However, the short half-life of most injected compounds in the vitreous, a few hours only, requires frequent administrations. Injection of an active drug in significant amounts in the posterior segment of the eye, especially intravitreally, implies a sudden and massive increase in their concentration in the vitreous and even anterior segment of the eye, and can also lead to undesirable and consequent local ocular side effects. For both reasons of short half life and possible toxicity if injected in a high amount, repeated intravitreal injections may be needed. However, repeated intravitreal injections are responsible of side effects such as intraocular infections, retinal detachment or cataracts. Moreover, these injections are poorly accepted by patients unable to deal with the pain and discomfort.

Some research on implant devices has been conducted in order to address these technical issues. For example, US20050244469 discloses a method for treating an ocular condition comprising the insertion of an implant into an ocular site of a patient with an ocular condition, more preferably in the vitreous body of the eye of a patient to treat a condition or disease of the posterior segment of the eye.

However, there is a need for alternative solutions for providing therapeutic treatment of an ocular condition, such as posterior ocular condition. In particular, there is still a need for treatment over an extended duration, for example, time periods extending up to 30 days, 60 days, 90 days, 120 days, 6 months, 8 months, 12 months or more. There is also a need to reduce the frequency of injections, such that the number of injection should be equal or less than once a month, preferably equal or less than once every 2 months, more preferably equal or less than once every three months, most preferably equal or less than once every four, five or six months.

A recognized advantage of providing a method for an extended treatment is to prevent recurrence of the inflammatory or other posterior ocular condition treated. It can also minimize the number of surgical interventions required by the patient over time to treat an ocular condition. From this assumption, Applicant searched alternative therapeutic pathways for an efficient administration of ophthalmic drugs inside the eye.

It is thus a goal of this invention to provide a sustained release of a therapeutically amount of an active agent for an extended duration as described hereabove, with a reduced amount of injections.

One further goal of this invention is to provide a composition, delivering a therapeutic amount of at least one active drug for a sustained period in the posterior segment of the eye, without any side effects. Preferably, the composition of the invention delivers a therapeutic amount of active drug in the disease site. More preferably, the composition of the invention delivers the therapeutic amount of drug needed to treat the very pathology of the patient. According to this embodiment, the composition of the invention is of great interest for personalized methods of treatment.

This invention also relates to the use of inactive prodrugs of ophthalmic active drugs for the preparation of a medicament or an ophthalmic composition intended for the treatment of an ocular condition or disease of a human being or an animal, said medicament or ophthalmic composition being administered by invasive means, preferably by intraocular injection, more preferably by intravitreal injection, for in-situ sustained release of a therapeutic effective amount of drug in the posterior segment of the eye.

More precisely, the invention relates to the use of prodrug for the manufacture of a medicament or an ophthalmic composition useful for treating an ocular disease affecting the posterior segment of the eye, in a subject in need thereof, wherein the prodrug is in the form of a composition injected into the vitreous body, and the frequency of injections does not exceed one injection per month, preferably the frequency of injection is once every two months, more preferably once every six months or less frequently.

The invention also relates to the use of a prodrug for providing extended duration of treatment of an ocular disease affecting the posterior segment of the eye, in a subject in need thereof, said use comprising administering an amount of a prodrug enabling the sustained release of a therapeutically amount of said drug for a duration of at least one month, preferably at least 2 months, more preferably at least six months.

As used herein, prodrug refers to a drug precursor which, following administration, release the drug in vivo via some chemical or physiological process. According to an embodiment of the invention the prodrug releases the drug by a biological reaction, such as enzymatic cleavage. The prodrug may be in combination with any suitable excipient, especially any excipient injectable in the vitreous body of the eye. By "prodrug" in the meaning of this invention is preferably meant an lipophilic derivative of an ophthalmic drug, preferably a lipophilic long-chain ester of an ophthalmic drug; according to an embodiment, said, lipophilic ester is a radical comprising an ester function COO, the carbon or the oxygen atom being linked to an alkyl or an alkenyl branched or linear chain of more than 10 carbons preferentially of more than 12 carbons, more preferably of more than 14 carbons, even more preferentially of 16 carbons or more; and the other of the carbon and the oxygen atom being linked to a function of the active drug; according to a preferred embodiment, the prodrug releases the active drug when it is in contact with at least one enzyme, preferably one esterase. Esterases are generally recognized as an heterogeneous group of enzymes. Among esterases, pseudocholinesterase and acetylcholine esterase may be members of the esterases acting in the posterior segment tissues. According to an embodiment, the prodrug of the invention does not include a phosphate group. The prodrugs of the invention are preferably lipophilic prodrugs, which means that they have a poor solubility in the vitreous body, making the vitreous body a storage for said prodrugs, with little diffusion. According to an embodiment, the aqueous solubility of the prodrug of the invention is of less than 120 µg/mL, preferably of less than 50 µg/mL and more preferably of less than 10 µg/mL.

According to a preferred embodiment of the invention, the prodrug does not have any direct therapeutic and/or physiologic effect, and is therefore called "inactive", whereas the drug released by hydrolysis of the prodrug does have a physiological therapeutic effect. On the contrary, by "active" drug, in the meaning of this invention, is meant a drug that has a direct therapeutic and/or biological or physiologic effect. Thus, a difference has to be made between drug or drug derivatives that are therapeutically directly effective, and are "active" drugs or drug derivatives in the meaning of this invention, versus "inactive" prodrugs of the invention.

Without being linked by a theory, the Applicant observed that the vitreous body contains a very limited amount of esterases. Thus, when injecting the lipophilic ester prodrug of the invention in the vitreous body, the rate of conversion to the drug is low, making the vitreous body be a storage for the prodrug. The Applicant proposes that the esterases may be situated on or around the affected tissues of the posterior segment of the eye, thus resulting in the conversion prodrug to drug at this location. Moreover, Applicant proposes that a pathology affecting the tissues of the posterior segment of the eye may correspond to higher amounts of esterases at the location of the pathology. Thus, injecting a prodrug in the vitreous may lead to both conversion of the prodrug into the drug at the very site of the pathology, in an extent corresponding to the amount of esterases, and thus to the severity of the pathology, and to keeping further storage of prodrug in the vitreous for further release.

According to an embodiment of the invention, the molar ratio of the prodrug to the drug, in the vitreous, two months after one single injection of said prodrug, is preferably more than 10, more preferably more than 30, and even more preferably more than 60.

According to another embodiment of the invention, the molar ratio of the prodrug to the drug, in the tissues of the posterior segment of the eye, such as for example choroid and retina, two months after one single injection of said prodrug, is preferably less than 60, preferably less than 30.

Advantageously, the prodrug is injected in the vitreous in an amount enabling the sustained release of a therapeutically amount of said drug for a duration of at least one month, preferably at least 2 months, more preferably at least 6 months.

According to an embodiment, the prodrug is injected with a frequency of one injection every two months. In this embodiment, the release of the prodrug and its transformation into the drug is such that a therapeutic amount of drug is present on the target site, for example retina or choroid, during two months, the prodrug being sustaineously released during this period of time.

According to another embodiment of the invention, the prodrug is injected with a frequency of at most one injection every four months, preferably at most one injection every six months, and even more preferably one injection every twelve months or even less frequently.

Preferably, the prodrug is within a composition, wherein said prodrug is in combination with any suitable excipient or carrier for ophthalmic use. According to a first embodiment, the carrier is oily. Examples of suitable oily carrier are mineral oils such as silicone, paraffin or vegetal oils such as medium chain triglycerides, castor oil, olive oil, corn oil, soybean oil, palm oil or any other oil suitable for intraocular injection. According to an embodiment of the invention, the weight ratio prodrug/oil in the composition of the invention is 0.04 to 0.3.

According to an embodiment of the invention, the composition comprises at least one prodrug as above-defined, in combination with any ophtalmologically acceptable excipient or carrier. The carrier may be selected from a surfactant solution, an ophtalmologically acceptable oil, phospholipid vesicles or oil-in-water emulsion or water-in-oil emulsion or any other suitable carrier about 20, at least about 30 or at least about 40 weight percent of the composition/emulsion, preferably 10% of the emulsion.

According to a preferred embodiment, the carrier is an emulsion, preferably an oil-in-water emulsion, more preferably an anionic emulsion. In the embodiment where the carrier is an anionic emulsion, it is preferred that said emulsion comprises colloid particles having an oily core surrounded by interfacial film, the film comprising surface active agents, lipids or both, at least part or the surface active agents or lipids in the interfacial film having negatively charged polar groups, and the colloid particles have a negative zeta potential. Preferably, the prodrug is comprised within the emulsion in an amount of about 0.01% to about 10% w/w of the composition. According to an embodiment, the prodrug is comprised in the amount of about 0.5% to about 3% w/w of the composition. In a preferred embodiment, the prodrug is comprised in an amount of about 2% w/w of the composition. In another preferred embodiment of the present invention, the prodrug is comprised in an amount of about 1% w/w of the composition. Excipient characteristics that are considered include, but are not limited to, the biocompatibility and biodegradability at the site of injection, compatibility with the prodrug of interest, and processing temperatures.

When the excipient or the carrier is an emulsion, according to an embodiment of the invention, the oil phase represents at least about 1, at least about 5, at least about 10, at least about 20, at least about 30 or at least about 40 weight percent of the composition. In a preferred embodiment, the oil represents 10 weight percent of the composition. In this embodiment, the composition includes at least one surfactant, preferably in an amount of 0.1-10% w/w of the composition. According to an embodiment, the surfactant is selected from phospholipids, poloxamers, tyloxapol, polysorbate, and polyoxyethylene fatty acid esters. In this embodiment, the composition preferably includes at least one isotonicity agent, preferably in an amount of 0.1-10% w/w of the composition. According to an embodiment, the isotonicity agent is glycerol.

Preferably, the composition of the invention is as follows:

| Role | Amount (w/w) |
| --- | --- |
| Prodrug | 0.01-10% |
| Oil | 1-40% |
| Surfactant | 0.1-10% |
| Tonicity agent | 0.1-10% |
| Dispersing medium | Up to 100% |

According to an embodiment, the composition of the invention is as follows:

| Role | Amount (w/w) |
| --- | --- |
| Prodrug | 0.1-5% |
| Oil | 8-12% |
| Surfactant | 0.5-2% |
| Tonicity agent | 1-3% |
| Dispersing medium | Up to 100% |

In an embodiment of the invention, the amount of prodrug to be administrated, preferably a lipophilic ester of dexamethasone, more preferably dexamethasone palmitate, is an amount therapeutically equivalent to 0.01-6 µmol, preferably 0.1-2.5 µmol, more preferably 0.15 to 1.3 µmol of drug, preferably dexamethasone.

In a further embodiment the molar amount of prodrug administered is higher than the highest non-toxic molar amount of corresponding injected by the same administration mode.

The Applicant performed a number of tests and noticed that the invention had the further advantage that he could not detect any release of drug in the plasma, which may mean that there is none or few passage of the drug released through the general system of the subject, and in any event, no related side effect is observed.

In the meaning of this invention, injecting in the vitreous body means performing an intravitreal injection.

According to the invention, the hydrolysis of the prodrug results in therapeutically amounts of drug at the targeted site of action, preferably at retina and/or choroid.

According to a preferred embodiment of the invention, the half-life of the prodrug in the target tissue is of at least 15 days, preferably of at least 30 days, preferably of at least 60 days, preferably of at least 6 months.

According to a preferred embodiment of the invention, the prodrug does not cause vision impairment or troubles.

The present invention intends to propose solutions for treating various ophthalmic or ocular conditions and diseases. The present invention is especially designed for the treatment of posterior ocular conditions, which means any disease, ailment or condition which primarily affects or involves a posterior ocular site such as choroid or sclera (in a position posterior to a plane through the posterior wall of the lens capsule), vitreous, vitreous chamber, retina, optic nerve (including the optic disc), and blood vessels and nerves which vascularize or innervate a posterior ocular site. A posterior ocular condition can include a disease, ailment or condition.

Examples of such conditions include without limitation Macular Disorders such as myopia, Non-Exudative Age Related Macular Degeneration (Dry), Exudative Age Related Macular Degeneration (Wet), Choroidal Neovascular Membranes (others than ARMD) and Cystoid Macular Edema; Inflammatory Disorders such as Uveitic Retinal Disease, Endophthalmitis, Toxoplasmic Retinochoroiditis, Systemic General Disorders Associated with Retinal Uveitis or Retinochoroidal Syndromes (Syphilis, Tuberculosis, Lyme Diseases, Chung Strauss Disease, LED, etc), Neuroretinitis, Optic Neuritis; Vascular Disorders such as Diabetic Retinopathy (all stages), Diabetic Macular Edema, Arterial Occlusion, Venous Occlusion; Heredo Retinal Dystrophies such as Stargardt's Disease, Fundus Flavimaculatus, other Heredomacular Dysropy; Trauma caused by Laser, photodynamic therapy, Photocoagulation, Hypoperfusion During Surgery; Macular Hole; Retinal Disease Associated with Tumors, Posterior Uveal Melanoma, Retinoblastoma and Choroidal Metastasis.

As used herein, "effective amount," and "sufficient amount" may be used interchangeably and refer to an amount of an ingredient which is sufficient to achieve an intended physiological effect. Thus, a "therapeutically effective amount" refers to a non-toxic, but sufficient amount of an active agent, to achieve therapeutic results in treating a condition for which the active agent is known to be effective. The determination of an effective amount is well within the ordinary skill in the art of pharmaceutical sciences and medicine, in that it may depend on various biological factors or individual variation and response to treatments.

As used herein, "subject" refers to a mammal that may benefit from the administration of a composition or method as recited herein. Most often, the subject will be a human but can be of any animals.

As used herein, "about" means approximately or nearly and in the context of a numerical value or range set forth herein means .+−0.10% of the numerical value or range recited or claimed.

As used herein, "administration," and "administering" refer to the manner in which a prodrug is presented to a subject.

As used herein, "invasive" refers to a form of administration that ruptures or punctures a biological membrane or structure with a mechanical means across which a prodrug is being delivered.

As used herein, "active agent" or "drug" may be used interchangeably to refer to an agent or substance that has measurable specified or selected physiologic activity when administered to a subject in a significant or effective amount. Examples of drugs useful in the present invention include without limitation: antivirals, chosen from the group comprising idoxuridine, trifluorothymidine, trifluorouridine, acyclovir, ganciclovir, cidofovir, interferon, DDI, AZT, foscamet, vidarabine, irbavirin; non-steroidal anti-inflammatories chosen from the group comprising amfenac, ketorolac, indomethacin, ibuprofen, diclofenac, flurbiprofen, piroxicam and other COX2 inhibitors; cytokines, interleukines and growth factors epidermal growth factor, fibroblast growth factor, pigment epithelium growth factor, platelet derived growth factor, transforming growth factor beta, ciliary neurotrophic growth factor, glial derived neurotrophic factor, NGF, EPO, PLGF, brain nerve growth factor (BNGF), vascular endothelial growth factor (VEGF) and monoclonal antibodies or proteins inhibiting the activity of such cytokines and growth factors; anti-inflammatories chosen from the group comprising alclometasone, amcinonide, amcinafel, amcinafide, beclamethasone, betamethasone, clobetasone, chloroprednisone, clocortelone, cortisol, C21-des-methyl-propionyl-ciclesonide, cortodoxone, difluorosone, descinolone, desonide, defluprednate, dihydroxycortisone, desoximetasone, dexamethasone, deflazacort, diflorasone, dichlorisone, fluazacort, flucetonide, flucloronide, fludrotisone, fluorocortisone, flumethasone, flunisolide, fluocinonide, fluocinolone, flucortolone, fluperolone, fluprednisolone, fluoroandrenolone, flurandrenolide, fluorametholone, fluticasone, hydrocortisone, hydrocortamate, loteprendol, medrysone, meprednisone, methylprednisone, methylprednisolone, mometasone, paramethasone, prednisolone, and triamcinolone, salts, derivatives, and a mixture thereof; anti-angiogenic compounds such as anecortave, combretastatin, vascular endothelial growth factor (VEGF) inhibitors, squalamine, AdPEDF, VEGF-traps; immunological response modifiers chosen from the group comprising mycophenolic acid, muramyl dipeptide, cyclosporins, interferons, interleukin-2, cytokines, tacrolimus, tumor necrosis factor, pentostatin, thymopentin, transforming factor beta.sub.2, erythropoetin; antineogenesis proteins; antibodies (monoclonal or polyclonal) or antibodies fragments, oligoaptamers, aptamers and gene fragments (oligonucleotides, plasmids, ribozymes, small interference RNA (SiRNA), nucleic acid fragments, peptides).

According to a first embodiment, this invention relates to a composition comprising a lipophilic long chain ester of at least one antiviral drug chosen from the group comprising idoxuridine, trifluorothymidine, trifluorouridine, acyclovir, ganciclovir, cidofovir, interferon, DDI, AZT, foscamet, vidarabine, irbavirin for the preparation of a medicament for treating ophthalmic conditions linked to viral infections, such as for example viral retinopathies.

According to an embodiment, hexadecyloxypropylcyclic cidofovir (HDP-Ccdv), 1-O-hexadecylpropanediol-3-phosphoganciclovir are excluded from the scope of the invention.

According to a second embodiment, this invention relates to a composition comprising a lipophilic long chain ester of at least one non-steroidal anti-inflammatory drug chosen from the group comprising amfenac, ketorolac, indomethacin, ibuprofen, diclofenac, flurbiprofen, piroxicam and other COX2 inhibitors; cytokines, interleukines and growth factors epidermal growth factor, fibroblast growth factor, pigment epithelium growth factor, platelet derived growth factor, transforming growth factor beta, ciliary neurotrophic growth factor, glial derived neurotrophic factor, NGF, EPO, PLGF, brain nerve growth factor (BNGF), vascular endothelial growth factor (VEGF) and monoclonal antibodies or proteins inhibiting the activity of such cytokines and growth factors for the preparation of a medicament for treating ophthalmic conditions linked to ophthalmic inflammations of the posterior segment of the eye.

According to a third embodiment, this invention relates to a composition comprising a lipophilic long chain ester of at least one anti-inflammatory drug chosen from the group comprising alclometasone, amcinonide, amcinafel, amcinafide, beclamethasone, betamethasone, clobetasone, chloroprednisone, clocortelone, cortisol, C21-des-methylpropionylciclesonide, cortodoxone, difluorosone, descinolone, desonide, defluprednate, dihydroxycortisone, desoximetasone, dexamethasone, deflazacort, diflorasone, dichlorisone, fluazacort, flucetonide, flucloronide, fludrotisone, fluorocortisone, flumethasone, flunisolide, fluocinonide, fluocinolone, flucortolone, fluperolone, fluprednisolone, fluoroandrenolone, flurandrenolide, fluorametholone, fluticasone, hydrocortisone, hydrocortamate, loteprendol, medrysone, meprednisone, methylprednisone, methylprednisolone, mometasone, paramethasone, prednisolone, and triamcinolone, salts, derivatives, and a mixture thereof; for the preparation of a medicament for treating ophthalmic conditions linked to ophthalmic inflammations of the posterior segment of the eye.

According to a preferred embodiment, the composition of the invention comprises a lipophilic long chain ester of steroid, such as for example dexamethasone palmitate.

According to a fourth embodiment, this invention relates to a composition comprising a lipophilic long chain ester of at least one antiangiogenic drug such as anecortave, combretastatin, vascular endothelial growth factor (VEGF) inhibitors, squalamine, AdPEDF, VEGF-traps; immunological response modifiers chosen from the group comprising mycophenolic acid, muramyl dipeptide, cyclosporins, interferons, interleukin-2, cytokines, tacrolimus, tumor necrosis factor, pentostatin, thymopentin, transforming factor beta.sub.2, erythropoetin; antineogenesis proteins; antibodies (monoclonal or polyclonal) or antibodies fragments, oligoaptamers, aptamers and gene fragments (oligonucleotides, plasmids, ribozymes, small interference RNA (SiRNA), nucleic acid fragments, peptides) for the preparation of a medicament for treating ophthalmic conditions linked to ophthalmic inflammations of the posterior segment of the eye.

According to an embodiment of the invention, the drug has an ophthalmic physiologic therapeutic activity, whereas the prodrug is inactive.

According to another embodiment of the invention the prodrug is a drug, or is prepared from a drug or is an ester of a drug, which has or was grafted with functional groups such as haloformyl, hydroxyl, aldehyde, alkyl, alkenyl, alkynyl, carboxamide, primary amine, secondary amine, tertiary amine, quaternary ammonium ion, azo (Diimide), benzyl, carboxylate, carboxyl, cyanate, thiocyanate, ether, ester, halo, primary ketimine, secondary ketimine, primary aldimine, secondary aldimine, isocyamide, isocyanate, isothiocyanate, ketone, nitrile, nitro, nitroso, peroxy, phenyl, phosphino, phosphate, phosphono, phosphate, pyridyl, sulfonyl, sulfo, sulfinyl or sulfhydryl groups.

According to an embodiment, the term composition should not be construed as an implantable device.

According to another embodiment, the composition of the invention is combined or is within an implantable device.

According to an embodiment of the invention, the enzyme involved in the transformation of the prodrug into the drug may be esterases, and possibly also:

Oxidoreductases acting on the CH, $CH_2$, CH—OH, aldehyde, oxo, CH—CH, CH—$NH_2$, CH—NH, sulfur, phosphorus, arsenic or heme groups of donors; oxidoreductases acting on NADH or NADPH; oxidoreductases acting on nitrogenous compounds, diphenols and related substances or hydrogen as donors; oxygenases; oxidoreductases acting on peroxide or superoxide radicals as acceptors; oxidoreductases acting on the iron-sulfur proteins as donors;

Transferases transferring one carbon, alkyl, aryl, nitrogenous, aldehyde or ketone groups; transferases; acyltransferases; glycosyltransferases; transferases transferring phosphorus-, selenium- or sulfur-containing groups;

Lyases such as carbon-carbon, carbon-oxygen, carbon-nitrogen, carbon-sulfur, carbon-halide or phosphorus-oxygen lyases.

Isomerases such as racemases and epimerases; intramolecular oxidoreductases; intramolecular transferases or intramolecular lyases;

Ligases forming carbon-oxygen, carbon-sulfur, carbon-nitrogen, carbon-carbon, phosphoric ester or nitrogen-metal bonds.

Preferred enzymes are hydrolases which act on ester or ether bonds; hydrolases acting on carbon-nitrogen, carbon-carbon, halide, phosphorus-nitrogen, sulfur-nitrogen, carbon-phosphorus, sulfur-sulfur or carbon-sulfur bonds; glycosylases; peptidases; hydrolases acting on acid anhydrides.

More preferred enzymes are esterases.

Preferred prodrugs are esters of drugs, wherein the ester group is of formula —COOR or —OC(O)R, or ether of drugs wherein the ester group is of formula OR, wherein R is a long alkyl or alkenyl chain, preferably a C4-C16 alkyl chain, even more preferably C12, C14, C16, C18, C20 saturated or unsaturated chain, more preferably any suitable lipophilic chain.

As used herein, alkyl means straight chain saturated hydrocarbon or branched saturated hydrocarbon. Preferred alkyl groups are those comprising more than 4 carbon atoms, preferentially more than 8 atoms, more preferentially more than 12 atoms. As used herein, alkenyl means linear or branched insaturated carbon chain.

Preferred alkenyl radicals comprise 10 carbon atoms or more, preferentially 12 carbon atoms or more, more preferentially 14 carbon atoms or more, even more preferentially 16 or 18 carbon atoms or more.

The invention is further illustrated by the following example, which should not be considered in any way as a limitation the scope of the protection.

EXAMPLE

1. Analytical Methods for Simultaneous Determination of Dexamethasone and Dexamethasone Palmitate in Ocular Tissues A liquid chromatographic-mass spectrometric method for the simultaneous determination of dexamethasone and dexamethasone palmitate in ocular tissues was developed. Analytes and internal standard (roxithromycine) were extracted from the tissues using acetonitrile and separated by reverse phase liquid chromatography with a C8 column and a gradient mobile phase. The compounds were detected by mass spectrometric detection (atmospheric pressure ionization) with selected ion monitoring (SIM) (393.0 for dexamethasone and 631.5 for dexamethasone palmitate). The method was selective for both compounds and the limits of quantification were 32.7 ng/g of retina and 71.6 ng/g choroid. The unweighed linear model was applied.

2. Intraocular Pharmacokinetics of Dexamethasone Palmitate and Dexamethasone Following Intravitreal Administration Methods:

One single unilateral injection of a 0.8% (8 mg/ml) dexamethasone palmitate emulsion was administered intravitreally (100 μL) to rabbits. Animals were sacrificed at days 1, 7, 14, 21, 28 or 60 days (n=4/timepoint). Dexamethasone (D) and dexamethasone palmitate (DP) in tissues were determined. All concentrations are expressed in ng/g.

| | | Day 1 | | Day 7 | | Day 14 | | Day 28 | | Day 60 | |
|---|---|---|---|---|---|---|---|---|---|---|---|
| | | Mean | sd | Mean | sd | Mean | sd | Mean | sd | Mean | sd |
| Retina | DP (nmol/g) | 106 | 74 | 93 | 38 | 136 | 19 | 146 | 109 | 55 | 37 |
| | D (nmol/g) | 7 | 2 | 11 | 4 | 6 | 4 | 4 | 1 | 2 | 2 |
| | DP/D | 15.14 | | 8.45 | | 22.6 | | 36.5 | | 25 | |
| Choroid | DP (nmol/g) | 191 | 69 | 103 | 77 | 22 | 11 | 143 | 61 | 52 | 22 |
| | D (nmol/g) | 12 | 6 | 12 | 7 | 9 | 4 | 4.2 | 1 | 3 | 2 |
| | DP/D | 15.91 | | 8.58 | | 2.44 | | 35.65 | | 17.33 | |
| Aqueous humor | DP (nmol/g) | ND | ND | ND | ND | ND | ND | ND | ND | 0 | 0 |
| | D (nmol/g) | ND | ND | ND | ND | ND | ND | ND | ND | 0 | 1 |

ND: Not determined.

Following IVT injection of a dose of 800 μg of prodrug, dexamethasone therapeutic levels of about 1000 ng/g were maintained for at least 2 months in the target tissues. Moreover, considerable amounts of the prodrug dexapalmitate remained in both retina and choroid, indicating an even more long-lasting release.

At the same time, the amounts of steroid in the vitreous and plasma were undetectable, suggesting fewer (if any) side effects in adjacent sites. This last fact was corroborated by IOP measurements, which were normal 2 months following the injection.

The invention claimed is:

1. A method for treating an ocular disease affecting the posterior segment of the eye selected from the group consisting of Exudative Age Related Macular Degeneration, Choroidal Neovascular Membranes and Cystoid Macular Edema, Inflammatory Disorders, Uveitic Retinal Disease, Vascular Disorders, Diabetic Retinopathy, Diabetic Macular Edema, Arterial Occlusion, Venous Occlusion, Heredo Retinal Dystrophies, and Stargardt's Disease, in a subject in need thereof,
   wherein a composition comprising about 0.01% to 10% w/w of a prodrug of a drug suitable for the treatment of said ocular disease, and medium chain triglycerides, is injected into the vitreous body, and the frequency of injections does not exceed one injection per month, said prodrug sustainingly releasing a drug in vivo,
   said release occurring by biological reactions at affected tissues of the posterior segment of the eye,
   the prodrug being a C4-C16 alkyl ester or ether of the drug,
   the drug being an anti-inflammatory selected from the group consisting of alclometasone dipropionate, amcinonide, amcinafel, amcinafide, beclamethasone, betamethasone, betamethasone dipropionate, betamethasone valerate, clobetasone propionate, chloroprednisone, clocortelone, cortisol, cortisone, cortodoxone, difluorosone diacetate, descinolone, desonide, defluprednate, dihydroxycortisone, desoximetasone, dexamethasone, deflazacort, diflorasone, diflorasone diacetate, dichlorisone, esters of betamethasone, fluazacort, flucetonide, fluchloronide, fludrotisone, fluorocortisone, flumethasone, flunisolide, fluocinonide, fluocinolone, fluocinolone acetonide, flucortolone, fluperolone, fluprednisolone, fluoroandrenolone acetonide, fluocinolone acetonide, flurandrenolide, fluorametholone, fluticasone propionate, hydrocortisone, hydrocortisone butyrate, hydrocortisone valerate, hydrocortamate, loteprendol, medrysone, meprednisone, methylprednisone, methylprednisolone, mometasone furoate, paramethasone, paramethasone acetate, prednisone, prednisolone, prednidone, triamcinolone acetonide, triamcinolone hexacatonide, and triamcinolone, salts, derivatives, and a mixture thereof, and
   the prodrug is not hexadecyloxypropylcyclic cidofovir or 1-O-hexadecylpropanediol-3-phosphoganciclovir.

2. The method according to claim 1, wherein two months after one injection of said prodrug, the drug cannot be detected in the vitreous or the molar ratio of the prodrug to the drug, in the vitreous, is more than 60.

3. The method according to claim 1, wherein the molar ratio of the prodrug to the drug, in the retina, two months after one injection of said prodrug, is less than 60.

4. The method according to claim 1, wherein the molar ratio of the prodrug to the drug, in the choroid, two months after one injection of said prodrug, is less than 60.

5. The method according to claim 1, wherein the prodrug is injected in the vitreous in an amount enabling the sustained release of a therapeutically amount of said drug for a duration of at least one month.

6. The method according to claim 1, wherein the prodrug is injected at most once every two months.

7. The method according to claim 1, wherein the prodrug is in combination with any suitable excipient or carrier suitable for ophthalmic use.

8. The method according to claim 1 wherein the prodrug is within an emulsion.

9. The method according to claim 1, wherein the prodrug is injected in the vitreous in an amount enabling the sustained release of a therapeutically amount of said drug for a duration of at least two months.

10. The method according to claim 1, wherein the prodrug is injected at most once every two months.

\* \* \* \* \*